US00PP13560P2

(12) United States Plant Patent
Bennerup

(10) Patent No.: US PP13,560 P2
(45) Date of Patent: Feb. 11, 2003

(54) ECHINACEA PLANT NAMED 'KIM'S MOP HEAD'

(76) Inventor: Pierre R. Bennerup, 1709 Kensington Rd., Kensington, CT (US) 06037

( * ) Notice: Subject to any disclaimer, the term of this patent is extended or adjusted under 35 U.S.C. 154(b) by 0 days.

(21) Appl. No.: 09/917,570

(22) Filed: Jul. 30, 2001

(51) Int. Cl.[7] ..... A01H 5/00
(52) U.S. Cl. ..... Plt./263
(58) Field of Search ..... Plt./263

(56) References Cited

U.S. PATENT DOCUMENTS

PP12,242 P2 * 12/2001 Hawks ..... Plt./263

OTHER PUBLICATIONS

UPOV ROM GTITM JOUVE Computer Database GTI JOUVE Retrieval Software, citation for 'Kim's Mop head'.*

* cited by examiner

*Primary Examiner*—Bruce R. Campell
*Assistant Examiner*—W C Haas

(57) ABSTRACT

*Echinacea purpurea* 'Kim's Mop Head' is a new and distinct dwarf perennial plant with white flowers and drooping ray petals on plants 35 to 40 cm tall, for an extended twelve weeks flowering period.

1 Drawing Sheet

BACKGROUND OF THE PLANT

The present invention relates to the new and distinct Coneflower plant, botanically known as *Echinacea purpurea* (L.) Moench hybrid and herein after referred to by the cultivar name 'Kim's Mop Head'. The stated cultivar is valued for its unique and long-lasting white flower display and short compact plant habit.

*Echinacea purpurea* 'Kim's Mop Head' is a selection of a non-induced whole plant mutation from a nursery propagated batch of Echinacea purpurea 'Kim's Knee High' U.S. Plant Pat. No. 12,242, discovered in one-gallon flowering pots by the inventor, Pierre Bennerup, at a nursery in Kensington, Conn. in the summer of 1996. 'Kim's Mop Head' has been propagated at a nursery in Kensington, Conn. by both tissue culture and root cuttings, and has demonstrated that the plant maintains its unique characteristics and is capable of reproducing identical individuals in successive generations. The claimed plant retains its distinctive characteristics and reproduces true to type in successive generations in both of the above-mentioned propagation methods.

SUMMARY OF THE INVENTION

*Echinacea purpurea* is one of two species in the genus. It is an American native plant found in the eastern United States region normally bounded by Michigan and Oklahoma on the west and Virginia, North Carolina and Georgia on the east. There are only a few white flowering varieties, including: 'Alba' (not patented), 'Cygnet White' (not patented). 'White Lustre' (not patented), and 'White Swan' (not patented). Among the purple or wine-colored flowering forms, one, *Rudbeckia purpurea* plant U.S. Plant Pat. No. 2,414 (now known as *Echinacea purpurea* 'Robert Bloom' U.S. Plant Pat. No. 2,414), is patented and another 'Kim's Knee High' U.S. Plant Pat. No. 12,242, has a more pink flower. The white flowering forms, 'Alba', 'White Lustre', and 'White Swan' are seed propagated, taller varieties, and like the species, flower in heights varying between 65 and 150 cm tall. One shorter variety, *Echinacea purpurea* 'Cygnet White', is a selection with white horizontal ray petals that reaches 52 cm in height. Other short, purple-flowering forms exist, such as 'Nana' (not patented) in Great Britain, and 'Rosenelf' (not patented) in Germany, and 'Kim's Knee High' (patent pending by another individual) with its pinkish red flower color. 'Kim's Mop Head' differs from all other Echinacea with a unique combination of traits. The plant is short and compact, flowering at no more than 40 cm. The flowers are pure white, and the petals droop as the flowers mature.

BRIEF DESCRIPTION OF DRAWINGS

The photographs of the new invention demonstrate the overall appearance of the plant including the unique traits. Light source direction may cause the appearance of variation in color. The colors are as accurate as reasonably possible with color reproductions.

DETAILED DESCRIPTION OF PLANT VARIETY

Figure 1:
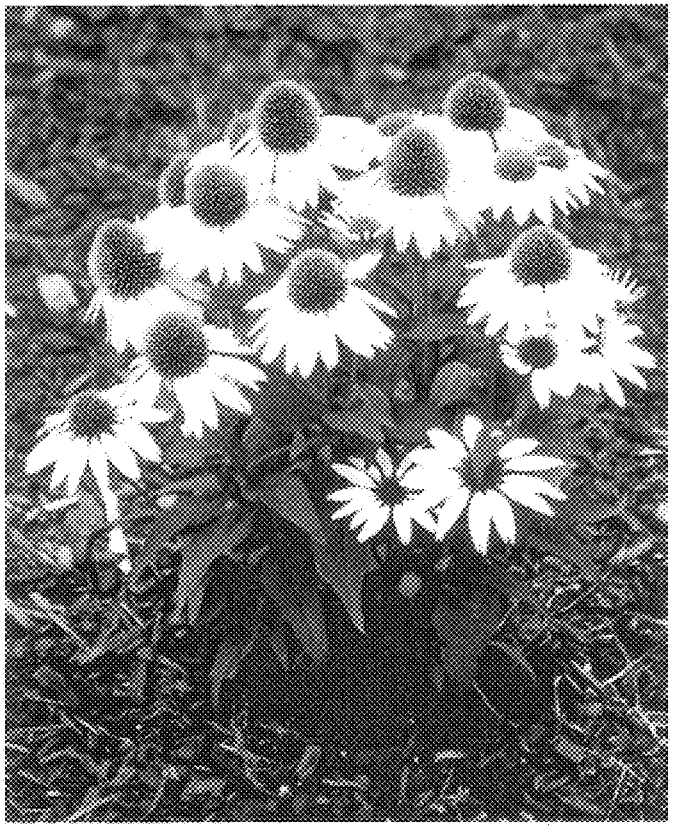
FIG. 1 shows the habit of a three-year-old plant in flower.
Figure 2:
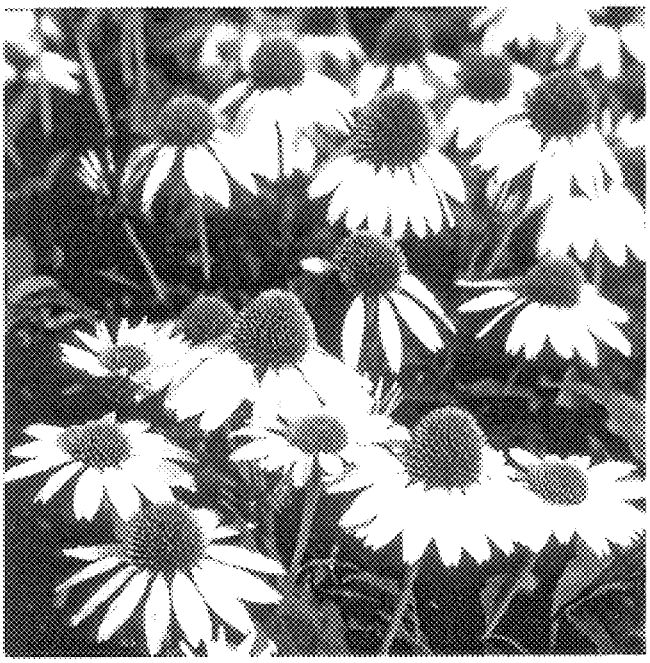
FIG. 2 shows a close-up view of some flowers to demonstrate flower color and form.

The following color description is based on color terminology in accordance with The Royal Horticultural Society Colour Chart and is labeled with RHS and the appropriate corresponding reference number and letter.

Echinacea 'Kim's Mop Head' is botanically known as *Echinacea purpurea* cultivar 'Kim's Mop Head'. The plant is a hardy herbaceous perennial that grows from zone 3 to 9 on the USDA Plant Hardiness Chart. It produces one to several multiple branched stems from a fibrous rooted crown or caudex. Stems or peduncles are up to 38 cm long and 6 mm in diameter. The hispid to hirsute stems are a light yellow green, about RHS 145 B to RHS 145 C. The basal leaves are 3 to 5 cm wide and up to 15 cm long. Each stem possesses seven to eight middle cauline leaves in an alternate pattern that are scabrous on both sides. The stem usually has one or seldom more alternate branches in the upper leaf axils. Peduncle is a light green RHS 145 C. Leaf blades are mostly toothed (especially on the lower leaves). Both basal and cauline leaves are attenuate to the base, or tapered down to 5 mm on the petiole to form a wing, lanceolate to lance-ovate. Approximate petiole length is 10 to 15 cm. Leaves and petioles are closest to RHS 141 A on both the adaxial and abaxial surfaces.

'Kim's Mop Head' flowers on peduncles 32 to 38 cm tall beginning in late June in Kensington, Conn. If cut back after flowering it will continue flowering sporadically until frost on peduncles that stay below 38 cm. In trial tests at a nursery in Kensington, Conn. and in Zeeland, Mich.. *Echinacea purpurea* 'Kim's Mop Head' has shown a prolonged flowering period of twelve weeks or more.

The flowers of *Echinacea purpurea* 'Kim's Mop Head' are solitary heads with up to 21 drooping, mostly bifid, white petals 3.5 to 4.5 cm long and 7 to 10 mm wide. While ray petals are still developing and upright, the petals are a light yellow RHS 1 C. The disk is about 3 to 4 cm in diameter and up to 3 cm tall. Bud size one week before petals are horizontal is approximately 2 cm in diameter. By the time the ray petals are horizontal they are pure white. The petals continue to expand and droop to about 40° to 60° below the horizon. Each flower has about 80 curled, imbricate sepals, with acute apex, nearest Yellow-Green RHS 146 A on the adaxial side, RHS 146 B on the abaxial side, to 3 mm wide at the base and between 10 and 14 mm long. The plant has between 360 and 500 disk florets that are near RHS 17 B when young and anthers have dehisced, and become RHS 160 A. Roots are freely branched and fibrous. Gynoecium is about 6 mm long with a split stigma 1 mm. Color is nearest to RHS 150 A at the proximal end, and becoming a greyed-red nearest RHS 178 B near the distal end. Andoecium is about 5 mm long with five filaments about 2 mm of clear white ending with long thin stamens 3 mm long and less than 0.5 mm wide. The stamens are about RHS 178 A. Pollen is a RHS 17 B, round, about 2/100 mm in diameter. The plant produces approximately 125 seeds per flower about 5 mm long, about 2 mm wide, and vary between light to medium tan in color. A three-year-old plant may have between 40 and 56 flowers per plant during the growing season. Each flower lasts on the plant at least three to four weeks.

Different environmental conditions or garden setting, as to sun exposure, heat, soil fertility, water availability, etc., may cause some epigenetic variation, but the plant remains genotypically stable. For example, leaves grown in heavy shade have more stretched petioles with deeper green color, and flower number and size is reduced.

The plants root from tissue culture in two to four weeks. Time required to finish plants from plugs in a one gallon nursery pot is about eight to ten weeks during the summer.

The plant is drought tolerant, and is not susceptible to any major pests or pathogens.

I claim:

1. A new and distinct dwarf cultivar of *Echinacea purpurea* plant named 'Kim's Mop Head', with white drooping flower petals, extended flowering period; and suitable for landscape, potted plant or cut flower, as herein illustrated and described.

* * * * *